United States Patent [19]
Toybin et al.

[11] Patent Number: 6,106,542
[45] Date of Patent: Aug. 22, 2000

[54] SURGICAL FORCEPS

[75] Inventors: Leonid Toybin; Irving J. Fishman; Victor Avigdor Grinshtein, all of Houston, Tex.

[73] Assignee: Microsurgical Laboratories, Inc., Houston, Tex.

[21] Appl. No.: 09/012,668

[22] Filed: Jan. 23, 1998

[51] Int. Cl.$^7$ .................................................... A61B 17/28
[52] U.S. Cl. ........................ 606/205; 606/206; 606/207
[58] Field of Search .................................. 606/205, 206, 606/207, 208, 209, 210, 138, 211, 131, 133, 51, 52; D28/155; D24/143; 81/142, 415; 433/159

[56] References Cited

U.S. PATENT DOCUMENTS

| | | | |
|---|---|---|---|
| 3,140,715 | 7/1964 | Whitton | 606/210 |
| 3,367,336 | 2/1968 | Eizenberg | 606/210 |
| 3,392,727 | 7/1968 | Hanlon | 606/210 |
| 3,815,609 | 6/1974 | Chester | 606/210 |
| 4,726,368 | 2/1988 | Morris | 606/205 |
| 5,047,046 | 9/1991 | Bodoia | 606/205 |
| 5,047,049 | 9/1991 | Salai | 606/205 |
| 5,312,420 | 5/1994 | Toso et al. | 606/138 |
| 5,501,698 | 3/1996 | Roth et al. | 606/205 |

*Primary Examiner*—Michael Buiz
*Assistant Examiner*—Lien Ngo
*Attorney, Agent, or Firm*—Paul N. Katz; Ronald L. Chichester; Frohwitter

[57] ABSTRACT

A surgical forceps adapted to grip tissue, blood vessels and walls of organs without causing injury thereto, and to further grasp suture needles without causing damage to the forceps. The surgical forceps is made of a light weight but strong material formed into two opposed branch arms joined at a proximate end and having springingly open opposing tips at a distal end. An alignment pin is attached to one of the branch arms and is located toward the distal end thereof. An alignment hole in the other branch arm is opposite the alignment pin and is comprised of a bushing made of a low friction material such as various types of plastics, NYLON™, TEFLON™ and the like. The alignment pin and bushing hole are located as close to the distal ends of the branch arms as physically practical. The alignment pin and bushing hole cooperate together in preventing the distal opposing tips from overlapping (misalignment). Stops are provided in a central portion of the branch arms to prevent excessive compression of the opposing tips which may result in misalignment thereof, tissue trauma or bowing. Platforms are provided proximate to the tips located at the distal ends of the branch arms of the forceps. The platforms are on opposing faces of the tips and distal portions of the branch arms, and are made from hard material. The platforms are adapted to allow a surgeon to grasp and withdraw a suture needle during surgery without damaging the delicate opposing tips normally used to grasp body tissues.

27 Claims, 7 Drawing Sheets

SURGICAL FORCEPS

BACKGROUND OF THE INVENTION

1. Field of the Invention

The present invention relates to surgical forceps adapted to grip tissue, blood vessels and walls of organs without causing injury thereto, and to further grasp suture needles without causing damage to the forceps.

2. Description of the Related Technology

In many surgical procedures (operation) the surgeon is required to hold, lift or displace tissue, blood vessels and/or walls of organs. During the operation the surgeon must positively grip tissue, blood vessels and/or walls of organs in a manner which causes as little damage thereto as possible. The surgeon typically uses surgical forceps to positively grip these tissues. The surgical forceps, generally, are tweezer shaped, have two branch arms joined at a proximate end, and have open opposing tips at an opposite distal end. The opposing tips are springingly biased open. The surgeon grasps the two branches together and must gently close the opposing tips so as to grasp the tissue, blood vessels and/or walls of organs without damage thereto.

The surgical forceps are designed to grip the tissue, blood vessels and/or walls of organs with a positive grip but with minimal trauma thereto. Various sizes of forceps (i.e., length and width) having different types of opposing tips may be utilized depending upon the type of operation, area of the body, the tissue, blood vessels and/or walls of organs involved. The opposing tips may comprise straight, curved, serrated, toothed, ring shapes, etc. The opposing tips also may be designed in various sizes depending on the intended use of the forceps.

Surgical forceps, generally, are made of stainless steel, or titanium. Titanium forceps are light in weight, corrosion resistant and very strong. Some surgical forceps have been designed with an alignment pin attached to one of the branch arms and adapted to mate with an opposing alignment hole in the other branch arm. The alignment pin and hole are biased toward the distal end of the forceps and are used for keeping the tips in alignment when pressed together. Generally, the alignment pin slidingly engages the alignment hole when the forceps branch arms are squeezed together. Depending upon the dimensional clearance of the pin and hole, and the coefficient of friction of the material comprising the alignment pin and hole, the frictional resistance may cause an increase in the squeeze force necessary to close the tips together. This increase in frictional resistance causes an unwanted loss of tactile feel to the surgeon of the tissues being manipulated during the operation. The weight of the forceps and the spring stiffness of the attached proximate end of the forceps also contribute to the tactile feel of the surgeon during manipulation of the tissues with the forceps.

Forceps are generally designed for manipulation of tissue, blood vessels and/or walls of organs during the surgical procedure. A needle holder is used to insert and withdraw a suture needle attached to suture thread. The opposing tips of the forceps must be designed for delicate non-traumatic manipulation of generally soft body tissues, while the needle holder must grasp a suture needle. Typically, however, during an operation a surgeon uses the forceps to withdraw a suture needle or the suture thread. Using the forceps to withdraw the suture needle will damage the delicate tissue handling tips and render the forceps useless for another operation.

The surgical forceps is designed for a balance between proper tip alignment and ease in squeezing the branch arms together. Proper tip alignment is obtained by the proximate ends of the branch arms being rigidity attached together. The wider and/or thicker the material joining together the proximate ends of the two branch arms, the better the branch arm alignment rigidity. However, when less material joins the two branch arms together, the feel of the forceps is more sensitive, i.e., less force is required to close and to hold the tissues.

The alignment pin and hole prevent overlapping (misalignment) of the opposing tips, but do not prevent excessive force from being applied to the opposing tips. The surgeon may grasp the forceps anywhere along its longitudinal axis, and depending upon the position of the surgeon's fingers on the branch arms, the pressure applied at the distal opposing tips may vary greatly. Spring tension of the branch arms and frictional components added by the alignment pin engaging the alignment hole also add to the unpredictability of the pressure applied to the distal opposing tips. Too much pressure inadvertently applied to the branch arms by the surgeon can cause trauma to the grasped tissues.

What is needed is a surgical forceps that can manipulate delicate tissues with minimal trauma thereto, yet have adequate traction, maintain correct alignment of the opposing tips over a wide range of closure pressures, and be resistant to damage when used to withdraw a suture needle.

OBJECTS OF THE INVENTION

It is therefore an object of the present invention to provide a surgical forceps that is used for manipulating soft tissues but will not be damaged if used to withdraw a suture needle.

It is another object to prevent misalignment of the tips of a surgical forceps.

It is a further object of the present invention to minimize trauma to delicate tissues, small blood vessels and neural tissues by inadvertently applying too much force to the opposing tips of the surgical forceps.

It is a further object to improve the tactile feel of the surgical forceps by a surgeon during a surgical procedure.

It is another object to reduce the frictional engagement of an alignment pin with an alignment hole of a surgical forceps for improved tactile feel during manipulation by a surgeon.

It is still another object of the present invention to provide surgical forceps in a plurality of lengths and a plurality of different types of tips in various sizes.

SUMMARY OF THE INVENTION

The above and other objects of the present invention are satisfied, at least in part, by providing a surgical forceps made of a light weight but strong material formed into two opposed branch arms joined at a proximate end and having springingly open opposing tips at a distal end. An alignment pin is attached to one of the branch arms and is located toward the distal end thereof. An alignment hole in the other branch arm is opposite the alignment pin and is comprised of a bushing made of a low friction material such as various types of plastics, NYLON™, TEFLON™ and the like. The alignment pin and bushing hole are located as close to the distal ends of the branch arms as physically practical. The alignment pin and bushing hole cooperate together in preventing the distal opposing tips from overlapping (misalignment).

The present invention further provides stops in a central portion of the branch arms to prevent excessive compression of the opposing tips which may result in misalignment thereof, tissue trauma or bowing of the tips when grasping a suture needle. A further embodiment of the present invention provides platforms proximate to the opposing tip faces which are located at the distal ends of the branch arms of the forceps. The platforms are made from a hard material and cover the opposing faces of the tips. The platforms are adapted to allow a surgeon to grasp and withdraw a suture needle during surgery without damaging the delicate opposing tips normally used to grasp body tissues.

Another embodiment of the present invention is a "double action" forceps having first and second opposed branch arms. The first opposed branch arms are joined at a proximate end. One end (proximate end) of the second opposed branch arms are attached to the distal ends of the first opposed branch arms by first hinge means such as, for example, interlocking tongue and groove with a fastening pin therethrough. The other end (distal end) of the second opposed branch arms comprise opposing tips. Between the proximate and distal ends of the second opposed branch arms is a crossover second hinge means which performs a cantilevered function of reducing the amount of squeeze force necessary for a given force presented at the distal tips. The ratio of force at the distal tips and the force at the proximate ends of the second opposed branch arms is equal to the ratio of the length from the proximate end of the second opposed branch arm to the crossover second hinge divided by the distance from the distal tip to the crossover second hinge. The cantilever action of the double action forceps reduces the amount of effort required by the surgeon to close the distal opposing tips when manipulating tissues or grasping a suture needle. Thus during a long operation, the double action forceps greatly reduces hand fatigue.

A stop is located on one or both of the opposing faces of either the first or second opposed branch arms proximate to the first hinge means. This stop is used to prevent excessive compression of the opposing tips which may result in misalignment thereof, tissue trauma, or bowing of the tips when grasping a suture needle. Platforms made of hard material may also be located on the faces of the opposing tips located at the distal ends of the second opposed branch arms. The double action forceps of the present invention does not need the above mentioned alignment pin and hole for maintaining the alignment of the distal opposing tips, the first and second hinge means provide adequate alignment thereof. Preferably, only one stop is required for preventing excessive force between the opposing tips.

The opposing faces of the distal tips of either embodiment of the present invention may be comprised of straight, curved, serrated, toothed, ring shapes, etc. The present invention contemplates all sizes and shapes of distal opposing tips for a surgical forceps, for example but not limitation, micro-forceps, tissue forceps, ring tip forceps, vascular tissue forceps, delicate forceps, DeBakey forceps and the like.

The platforms on the faces of the opposing tips are made of hard material such as, for example but not limitation, tungsten carbide, carbide steel, diamond coating, epoxy, structurally reinforced epoxy, ceramic coating and the like. The platforms may be attached to the inside faces of the opposing tips at the distal portions of the branch arms by welding, adhesives, plating, coating, electroplating, chemical vapor deposition, ion bombardment, or any means that can effectively attach, coat or plate the hard platforms material to selected portions of the opposing inside faces of the branch arms proximate to the distal opposing tips.

The alignment pin generally is made of the same material as the branch arms, however, it may be made of a different material and pressed into or otherwise fixedly attached to one of the branch arms. The alignment hole bushing is made from a low friction material as described above and may be pressed into or otherwise attached to the other opposing branch arm. The advantage of the low friction material hole bushing is that the alignment pin engages this bushing without introducing an abrupt change of force required to close the branch arms together. This results in smoother operation of the present invention by the surgeon, thus giving the surgeon better tactile feel with the forceps during the surgical procedure. The alignment pin and/or hole bushing may be adapted for self alignment by a taper, bevel, radius and the like on the tip portion of the alignment pin and/or entry portion of the hole bushing. Preferably, the alignment pin and hole bushing are placed as close to the opposing tips of the forceps as physically possible. The only limitation being the amount of material necessary to contain (surround) the hole bushing. The pin, being smaller than the outside diameter of hole bushing, is not a limiting factor in placement thereof. The hard material platforms are generally located on the faces of the opposing tips and a distal portion of the opposed branch arms.

The opposed branch arms are made from a light weight and strong material, for example but not limitation, stainless steel, titanium, graphite fiber composite, reinforced synthetic resin, etc. Titanium is stronger and lighter in weight than stainless steel for a given size forceps. The hard material platforms protect the inside surfaces of the tips and a distal portion of the branch arms from other hard metals such as the suture needles. The low friction alignment hole bushing prevents frictional disruption of the smoothness when squeezing the opposed branch arms together by the surgeon. This is especially advantage when the branch arm material is titanium. Central portions of the outside surfaces of the branch arms may have a non-slip treatment applied thereto. This non-slip treatment may be machined or etched knurling and the like on the outside surface of the branch arms. The proximate ends of the opposed branch arms may be fixedly attached together by welding, gluing, pressing, pins, screws, or other attachment means known in the art of fastening materials together. The fixedly attached proximate ends of the branch arms also create a spring action which biases apart the distal ends (tips) of the branch arms. By selecting the amount of material and dimensional width of the attached proximate ends of the branch arms, the amount of compression pressure required to close the distal ends of the branch arms may be controlled.

Two stops are preferably located on the inside faces of the central portions of the branch arms and may be machined from the branch arm material or may be attached thereto in a separate step. The two stops prevent closing the branch arms less than a desired distance. The height or thickness of the stops determine the desired distance. The stops prevent excessive compression of the tips. Excessive compression can cause overlapping (misalignment) of the tips. The stops, by preventing excessive compression of the tips, greatly reduce the possibility of tissue trauma. The two stops are preferably located at the central portions of the branch arms, and also prevent the distal ends of the branch arms from "bowing" apart if excessive pressure is inadvertently applied to the branch arms, e.g., when grasping a suture needle.

In the double action embodiment of the present invention, hinged portions having moveable articulation confined to only one plane eliminates the necessity of the alignment pin and hole. In addition, preferably only one stop is needed to prevent closing the distal ends of the branch arms less than the desired distance. The hinged portions of the double action forceps may be designed for smooth yet rigid operation of the opposed first and second branch arms.

Other and further objects, features and advantages will be apparent from the following description of presently preferred embodiments of the invention, given for the purpose of disclosure and taken in conjunction with the accompanying drawings.

DETAILED DESCRIPTION OF THE PREFERRED EMBODIMENTS

Figure 1:
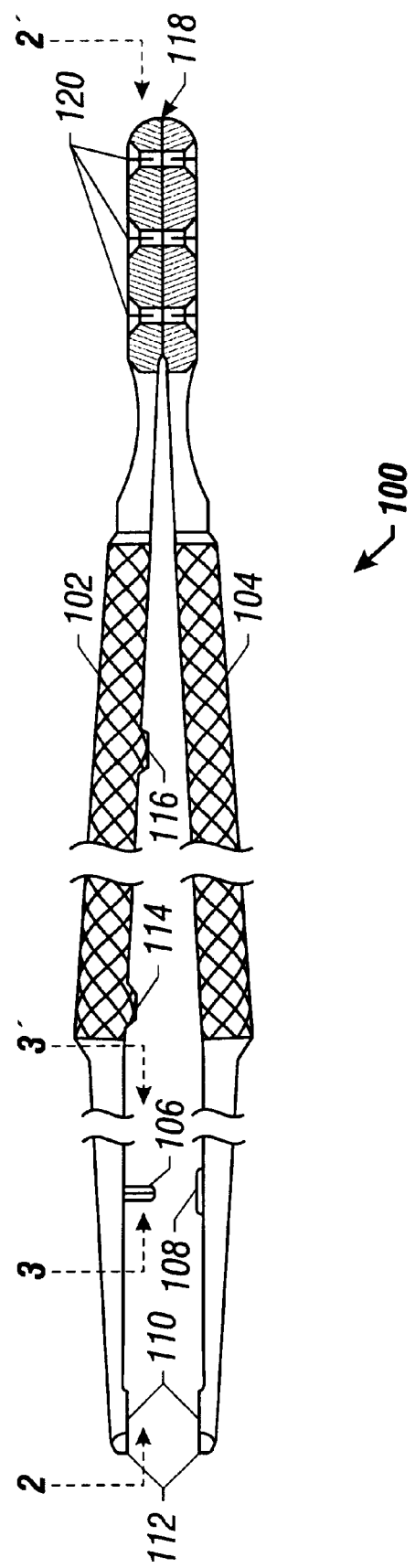
FIG. 1 is a schematic plan view of an embodiment of a surgical forceps, according to the present invention.

The present invention is a surgical forceps that can manipulate delicate tissues with minimal trauma thereto, yet have adequate traction, maintain correct alignment of the opposing tips over a wide range of closure pressures, and be resistant to damage when used to withdraw a suture needle.

Referring now to the drawings, the details of preferred embodiments of the present invention are schematically illustrated. Like elements in the drawings will be represented by like numbers, and similar elements will be represented by like numbers with a different lower case letter suffix.

Figure 2:
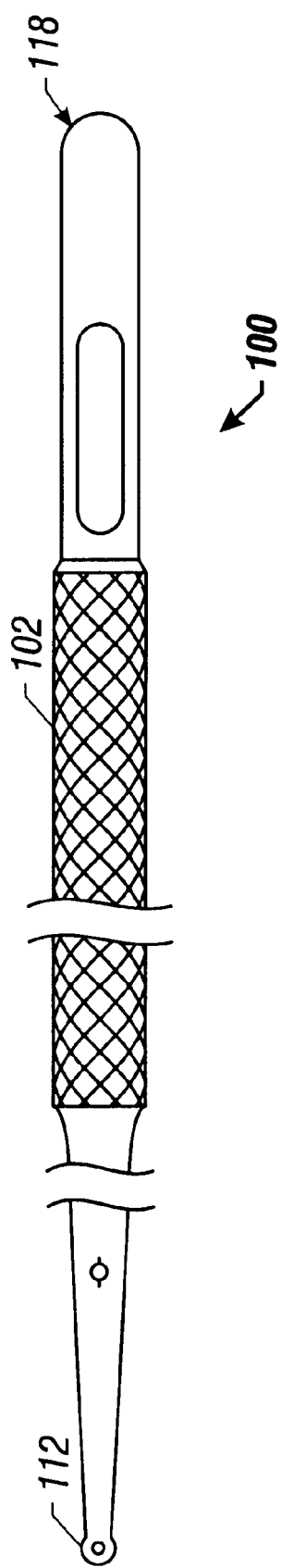
FIG. 2 is a schematic elevational view of the surgical forceps illustrated in FIG. 1.

Referring to FIGS. 1 and 2, schematic plan and elevational views of an embodiment of a surgical forceps are illustrated, according to the present invention. The surgical forceps is generally indicated by the numeral 100 and comprises a branch arms 102 and 104, an alignment pin 106, an alignment hole bushing 108, platforms 110, opposing tips 112, and stops 114 and 116. Proximate ends 118 of the branch arms 102 and 104 are fixedly attached together with pins 120 and are then welded together. Any means of fixedly attaching the proximate ends 118 of the branch arms 102 and 104 are contemplated herein. The proximate ends 118 are fixedly attached together such that the tips 112 of the branch arms 102 and 104 are springingly biased apart. Force placed on both sides of the central portions of the branch arms 102 and 104 will urge the opposing tips 112 together. This force is from a surgeon's fingers squeezing together the branch arms 102 and 104, for example, during a surgical procedure.

Figure 4A:
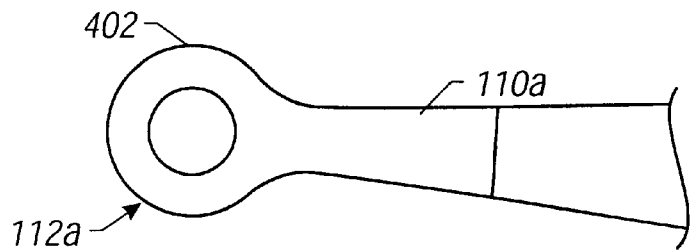
FIGS. 4A, 4B and 4C are schematic elevational views of various tips according to the present invention.
Figure 4B:
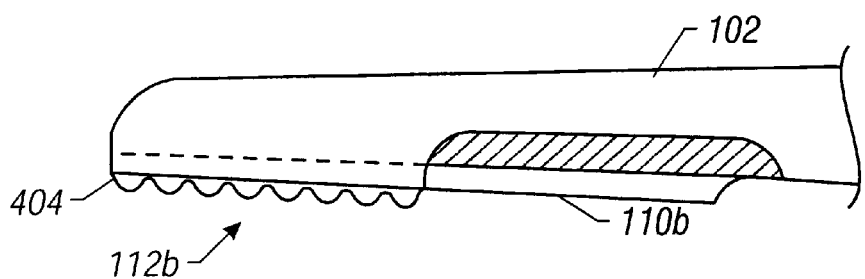
Figure 4C:
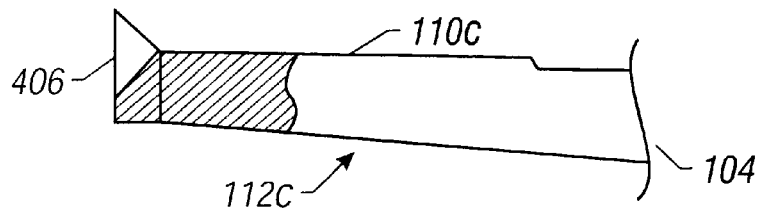

The opposing tips 112 may comprise straight, curved, serrated, toothed, ring shapes, etc., and may be designed in various sizes depending on the intended use of the forceps 100. For example but not limitation, a ring tip 402 for opposing tips 112a is illustrated in FIG. 4A, a DeBakey tip 404 for opposing tips 112b is illustrated in FIG. 4B, and a 1×2 teeth tip 406 for opposing tips 112c is illustrated in FIG. 4C, Proximate to the opposing tips 112 are platforms 110 (see also FIGS. 4B and 4C, platforms 110b and 110c).

The platforms 110 are made from hard material such as hard stainless steel, tungsten carbide, tungsten carbide plate insert, carbide steel, diamond coating, epoxy, structurally reinforced epoxy, ceramic coating and the like. The platforms 110 may be attached by welding, adhesives, plating, coating, electroplating, chemical vapor deposition, ion bombardment, or any means that can effectively attach, coat or plate the hard material to selected portions of the opposing inside faces of the tips 112 and distal portions of the branch arms 102 and 104 proximate to the opposing tips 112. The platforms 110 allow a surgeon to withdraw a suture needle (not illustrated) with the forceps 100 without damage thereto. The surgeon grasps the suture needle between the hard material platforms 110 instead of with the opposing tips 112, thus preventing damage to the delicate tips 112.

Figure 3:
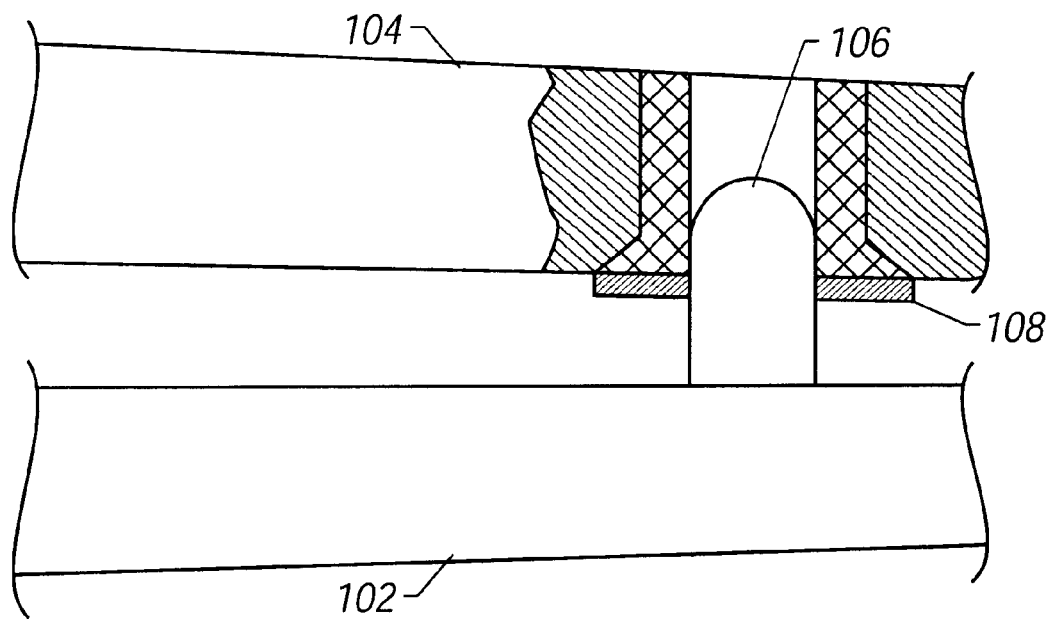
FIG. 3 is a schematic sectional view of a portion of the forceps illustrated in FIG. 1 taken along section lines 3—3.

Referring to FIG. 3, the alignment pin 106 generally is made of the same material as the branch arm 102, however, it may be made of a different material and pressed into or otherwise fixedly attached to the branch arm 102. The alignment hole bushing 108 is made from a low friction material as described above and may be pressed into or otherwise attached to the branch arm 104. The advantage of the low friction material hole bushing is that the alignment pin engages this bushing without introducing an abrupt or noticeable change of force required to close the branch arms 102 and 104 together. This is especially important when using titanium material and results in smoother operation of the present invention by the surgeon, thus giving the surgeon better tactile feel with the forceps during the surgical procedure. The alignment pin 106 and/or the hole bushing 108 may be adapted for self alignment by a taper, bevel, radius and the like on the tip portion of the alignment pin 106 and/or entry portion of the hole bushing 108. Preferably, the alignment pin 106 and hole bushing 108 are placed as close to the opposing tips 112 of the forceps 100 as physically possible. The only limitation being the amount of material necessary in the branch arm to contain (surround) the hole bushing 108.

The stops 114 and 116 are located on the inside faces of the central portions of one or to both of the branch arms 102 and 104, and may be machined from the branch arm material or may be attached thereto in a separate step. The stops 114 and 116 prevent closing the branch arms 102 and 104 less than a desired distance. The height or thickness of the stops 114 and 116 determine the desired distance. The two stops 114 and 116 prevent excessive compression of the opposing tips 112, and also prevent the tips 112 from "bowing" apart if excessive pressure is inadvertently applied thereto, e.g., when grasping a suture needle.

Figure 5:
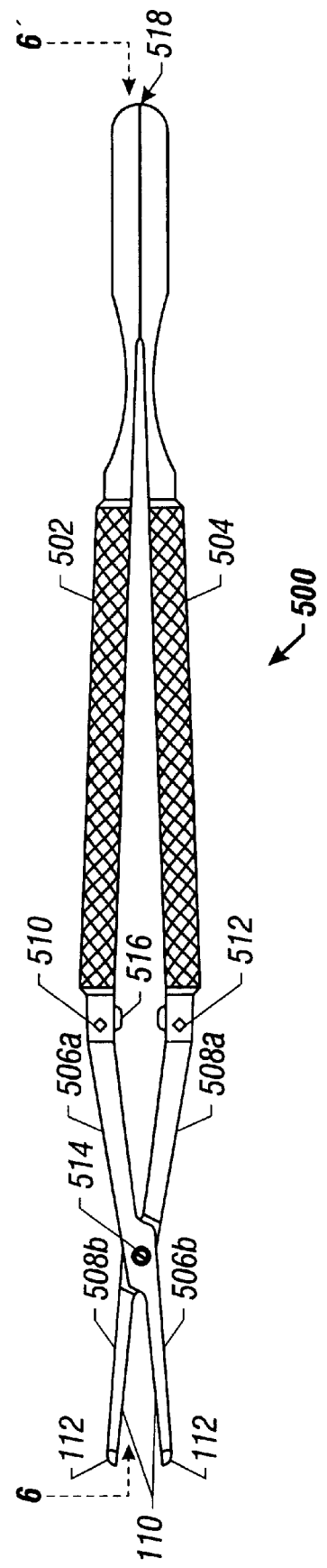
FIG. 5 is a schematic plan view of a double action surgical forceps, according to the present invention.
Figure 6:
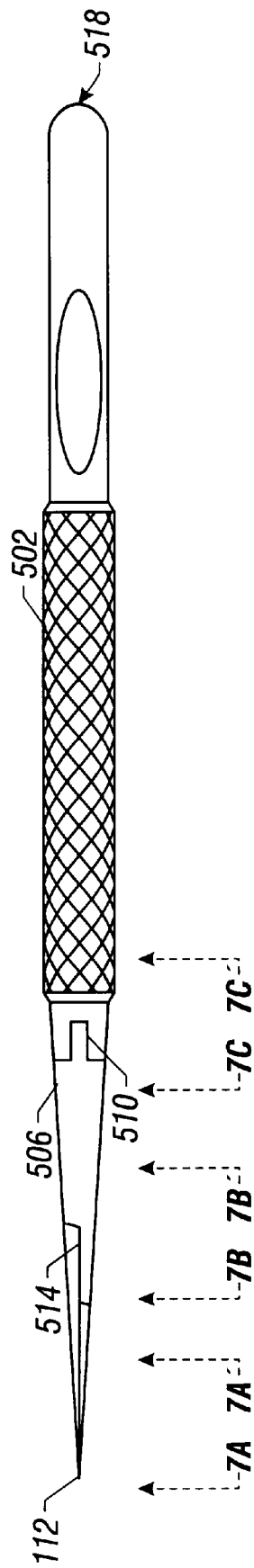
FIG. 6 is a schematic elevational view of the double action surgical forceps illustrated in FIG. 5.

Referring to FIGS. 5 and 6, schematic plan and elevational views of an embodiment of a double action surgical forceps are illustrated, according to the present invention. The double action surgical forceps is generally indicated by the numeral 500 and comprises first branch arms 502 and 504, second branch arms 506 and 508, first hinges 510 and 512, second hinge 514, platforms 110, opposing tips 112, and stop 516. Proximate ends 518 of the first branch arms 502 and 504 are fixedly attached together as described above. The proximate ends 518 are attached together such that the first branch arms 502 and 504 are springingly biased apart. Force placed on both sides of the central portions of the first branch arms 502 and 504 will urge them together. The second branch arms 506 and 508 are pivotally attached to the first branch arms 502 and 504 by the first hinges 510 and 512, respectively. Movement of the first hinges 510 and 512 are confined to one plane. The second hinge 514 pivotally attaches together the second branch arms 506 and 508. Movement of the second hinge 514 is confined to one plane.

When the first branch arms 502 and 504 are squeezed together the opposing tips 112 come together. An advantage of the double action forceps 500 is that the pressure exerted on the first branch arms 502 and 504 may be amplified in relation to the force being applied at the opposing tips 112. The proximate portions of the second arms 506a and 508a are attached to the first hinges 510 and 512, and he distal portions of the second arms 506b and 508b are at the tips 112 of the double action forceps 500. The ratio of the length of the proximate portion of a second arm 506a divided by the length of the distal portion of the second arm 506b determines the amplification of the force applied by the surgeon at the central portion of the forceps 500 to the resulting force being applied at the opposing tips 112. The double action forceps 500 reduces the amount of effort required by the surgeon to close the distal opposing tips 112 when manipulating tissues and suture needles, thus during a long operation the double action forceps 500 greatly reduces hand fatigue.

The stop 516 may be located on either one or both of the inside faces of the first branch arms 502 and/or 504, and may be machined from the branch arm material or may be attached thereto in a separate step. The stop 516 prevents closing the first branch arms 502 and 504 less than a desired distance. The height or thickness of the stop 516 determines the desired distance. The stop 516 prevents excessive compression of the opposing tips 112 and unwanted bowing thereof.

Figure 7C:
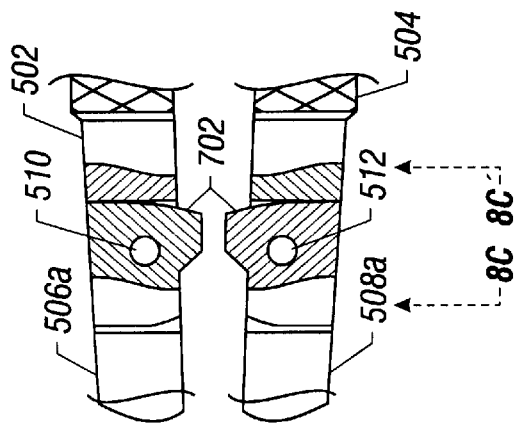
FIGS. 7A, 7B and 7C are schematic partial views of the double action forceps illustrated in FIG. 6 and taken along section lines 7A—7A, 7B—7B and 7C—7C, respectively.
Figure 7B:
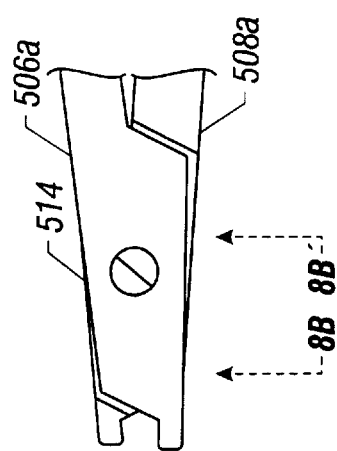
Figure 7A:
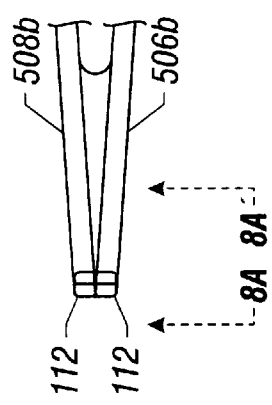
Figure 8C:
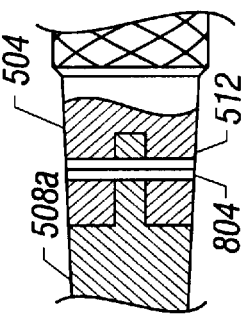
FIGS. 8A, 8B and 8C are schematic partial views of FIGS. 7A, 7B and 7C taken along section lines 8A—8A, 8B—8B and 8C—8C, respectively.
Figure 8B:
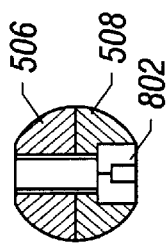
Figure 8A:
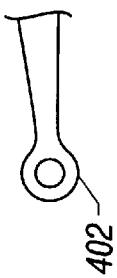

Referring to FIGS. 7A—7C and 8A—8C, schematic partial views of the double action forceps 500 are illustrated. FIGS. 7A and 8A illustrate a ring tip 402, however, any type of surgical forceps tip is contemplated herein for the present invention. FIG. 7B illustrates the second hinge 514 and FIG. 8B illustrates a cross-sectional cutaway view of a screw 802 pivotally attaching together the second branch arms 506 and 508. Referring to FIGS. 7C and 8C, the first hinges 510 and 512 are illustrated in schematic cross-sectional cutaway partial views. The first and second branch arms may be attached together with pin axles 804 or any other means that allow pivoting in one plane of the first and second branch arms. Stops 702 prevent the first branch arms 502 and 504 from opening too wide, which in turn, determines how wide apart the opposing tips 112 will be when no force is applied to the first branch arms 502 and 504 by the surgeon.

The present invention, therefore, is well adapted to carry out the objects and attain the ends and advantages mentioned, as well as others inherent therein. While the present invention has been depicted, described, and is defined by reference to particular preferred embodiments of the invention, such references do not imply a limitation on the invention, and no such limitation is to be inferred. The invention is capable of considerable modification, alternation, and equivalents in form and function, as will occur to those ordinarily skilled in the pertinent arts. The depicted and described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A surgical forceps assembly, comprising:

first and second branch arms joined at proximal ends thereof so that distal ends thereof are springingly biased apart;

first and second opposing tips, the first opposing tip at the distal end of the first branch arm, and the second opposing tip at the distal end of the second branch arm, wherein the first and second opposing tips are made of a first material;

first and second platforms located on inside faces of the first and second opposing tips and portions of the distal ends of the first and second branch arms proximal to the first and second tips, respectively, wherein the first and second platforms are adapted to grasp a suture needle, wherein the first and second platforms are made from a second material and the second material is harder than the first material;

an alignment pin attached perpendicular to a long axis of the first branch arm;

an alignment bushing having a hole therein is incorporated into the second branch arm;

the alignment pin and alignment bushing being positioned close to the distal ends of the first and second branch arms, and placed so as to engagingly cooperated together such that the alignment pin fits into the hole of the alignment bushing, wherein the first and second opposing tips cannot crossover each other; and first and second stops on an inside face of a central portion of the first branch arm, the first and second stops limiting how close the first and second branch arms come together, whereby a certain pressure between the first and second tips is not exceeded.

2. The surgical assembly of claim 1, wherein the first and second branch arms are made of light and strong material.

3. The surgical forceps assembly of claim 1, wherein the first and second branch arms are made of titanium.

4. The surgical forceps assembly of claim 1, wherein the first and second platforms are made of tungsten carbide plate.

5. The surgical forceps assembly of claim 1, wherein the first and second platforms are made of a coating of tungsten carbide.

6. The surgical forceps assembly of claim 1, wherein the first and second platforms are made of hard stainless steel.

7. The surgical forceps assembly of claim 1, wherein the first and second platforms made of a coating of diamond.

8. The surgical forceps assembly of claim 1, wherein the first and second platforms are ceramic.

9. The surgical forceps assembly of claim 1, wherein the first and second platforms are made of epoxy.

10. The surgical forceps assembly of claim 1, wherein the alignment bushing is made of a low friction material.

11. The surgical forceps assembly of claim 1, wherein the alignment pin tip is beveled.

12. The surgical forceps assembly of claim 1, wherein the alignment pin tip is rounded.

13. The surgical forceps assembly of claim 1, wherein the alignment pin tip is tapered.

14. The surgical forceps assembly of claim 1, wherein the alignment bushing hole is beveled.

15. The surgical forceps assembly of claim 1, wherein the alignment bushing hole is rounded.

16. The surgical forceps assembly of claim 1, wherein the alignment bushing hole is tapered.

17. The surgical forceps assembly of claim 1, wherein the first and second opposing tips are ring shaped.

18. The surgical forceps assembly of claim 1, wherein the first and second opposing tips have at least one tooth.

19. The surgical forceps assembly of claim 1, wherein the first and second opposing tips have a plurality of teeth.

20. The surgical forceps assembly of claim 1, wherein the first and second opposing tips are serrated.

21. The surgical forceps assembly of claim 1, wherein the first and second opposing tips are flat.

22. A double action surgical forceps assembly, comprising:
   first and second branch arms joined at proximal ends thereof so that distal ends thereof are springingly biased apart;
   third and fourth branch arms rotatably attached together;
   proximal ends of the third and fourth branch arms are rotatably attached to the distal ends of the first and second branch arms, wherein the first and second opposing tips are made of a first material;
   first and second opposing tips, the first opposing tip at the distal end of the third branch arm, and the second opposing tip at the distal end of the fourth branch arm, wherein the first and second opposing tips are made of a first material;
   first and second platforms located on insides faces of the first and second opposing tips and portions of the distal ends of the third and fourth branch arms proximal to the first and second tips, respectively, wherein the first and second platforms are adapted to grasp a suture needle, wherein the first and second platforms are made from a second material and the second material is harder than the first material; and
   a stop on an inside face of the first branch arm toward the distal end thereof, the stop limiting how close the first and second branch arms come together, thereby limiting how close the third and fourth branch arms come together, whereby a certain pressure between the first and second tips is not exceeded.

23. The double action surgical forceps assembly of claim 22, wherein the third and fourth branch arms are rotatably attached equidistant between the proximal and distal ends thereof.

24. The double action surgical forceps assembly of claim 22, wherein the third and fourth branch arms are rotatably attached toward the distal ends thereof.

25. The double action surgical forceps assembly of claim 22, wherein the third and fourth branch arms are rotatably attached toward the proximal ends thereof.

26. The surgical forceps assembly of claim 1, wherein said first and second platforms are made from corrosion resistant material.

27. The surgical forceps assembly of claim 1, wherein the difference between the height of the first and second platforms and the height of the first and second opposing tips is smaller than about one half the diameter of the suture needle to be grasped.

* * * * *